United States Patent
Kooyman

(10) Patent No.: US 12,194,019 B2
(45) Date of Patent: Jan. 14, 2025

(54) COMPOSITIONS AND METHODS FOR TREATING PAIN WITH WOGONIN

(71) Applicant: BRIGHAM YOUNG UNIVERSITY, Provo, UT (US)

(72) Inventor: David Lee Kooyman, Salem, UT (US)

(73) Assignee: Brigham Young University, Provo, UT (US)

(*) Notice: Subject to any disclaimer, the term of this patent is extended or adjusted under 35 U.S.C. 154(b) by 0 days.

(21) Appl. No.: 18/491,644

(22) Filed: Oct. 20, 2023

(65) Prior Publication Data
US 2024/0082209 A1    Mar. 14, 2024

Related U.S. Application Data

(63) Continuation of application No. 16/961,186, filed as application No. PCT/US2019/012869 on Jan. 9, 2019, now abandoned.

(60) Provisional application No. 62/756,188, filed on Nov. 6, 2018, provisional application No. 62/615,072, filed on Jan. 9, 2018.

(51) Int. Cl.
| | |
|---|---|
| *A61K 31/352* | (2006.01) |
| *A61K 9/00* | (2006.01) |
| *A61K 9/06* | (2006.01) |
| *A61K 9/14* | (2006.01) |
| *A61K 45/06* | (2006.01) |
| *A61K 47/10* | (2017.01) |
| *A61K 47/20* | (2006.01) |
| *A61K 47/44* | (2017.01) |
| *A61P 19/02* | (2006.01) |

(52) U.S. Cl.
CPC .......... *A61K 31/352* (2013.01); *A61K 9/0014* (2013.01); *A61K 9/06* (2013.01); *A61K 45/06* (2013.01); *A61K 47/10* (2013.01); *A61K 47/20* (2013.01); *A61K 47/44* (2013.01); *A61P 19/02* (2018.01)

(58) Field of Classification Search
CPC ...... A61K 31/325; A61K 9/0014; A61K 9/06; A61K 45/06; A61K 47/10; A61K 47/20; A61K 47/44; A61P 19/02
See application file for complete search history.

(56) References Cited

U.S. PATENT DOCUMENTS

| | | |
|---|---|---|
| 8,143,313 B2 | 3/2012 | Kubow et al. |
| 9,579,357 B1 | 2/2017 | Tobin et al. |
| 2005/0113405 A1 | 5/2005 | Harnish et al. |
| 2005/0119269 A1 | 6/2005 | Rao et al. |
| 2008/0145461 A1* | 6/2008 | Gonzalez ............ A61K 36/534 424/747 |
| 2009/0117061 A1* | 5/2009 | Gross ....... A61K 8/31 514/474 |
| 2009/0131889 A1 | 5/2009 | Oronsky et al. |
| 2013/0136811 A1* | 5/2013 | Schachter ............... A61P 25/00 549/403 |
| 2016/0184341 A1 | 6/2016 | Johnson |
| 2016/0296582 A1* | 10/2016 | Kapadia ............... A61K 36/752 |
| 2017/0071889 A1 | 3/2017 | Regis |
| 2021/0052543 A1 | 2/2021 | Kooyman |

FOREIGN PATENT DOCUMENTS

| | | |
|---|---|---|
| CN | 101700249 A | 5/2010 |
| CN | 101837003 A | 9/2010 |
| JP | 2007182384 A | 7/2007 |
| JP | 2008504336 A | 2/2008 |
| JP | 2017537073 A | 12/2017 |
| WO | 1998027975 A1 | 7/1998 |
| WO | 2003015766 A1 | 2/2003 |
| WO | 2011150175 A2 | 12/2011 |
| WO | 2016118866 A1 | 7/2016 |
| WO | 2017194586 A1 | 11/2017 |

OTHER PUBLICATIONS

Extended European Search Report for European Application No. 19738923.2, dated Nov. 16, 2021, 10 pages.
Notice of Reasons for Rejection for Japanese Application No. 2020-538049 with English translation, dated Oct. 19, 2022, 16 pages.
Communication Under Rule 71(3) EPC for European Application No. 19738923.2, dated Nov. 22, 2023, 49 pages.
Khan Nazir M. et al: "Wogonin. a natural flavonoid. intercalates with genomic DNA and exhibits protective effects in IL-1[beta] stimulated osteoarthritis chondrocytes", Chemico-Biological Interactions., vol. 274. Aug. 1, 2017 (Aug. 1, 2017). pp. 13-23. XP055858397, IR; ISSN: 0009-2797, DOI: 10.1016/j.cbi.2017.06.025.
Park et al., Chondroprotective Effects of Wogonin in Experimental Models of Osteoarthritis in vitro and in vivo. Biomolecules and Therapeutics, 2015, vol. 23, No. 5, pp. 442-448.
International Search Report dated May 8, 2019 for PCT/US2019/012869.
Hou et al., The Inhibitory Effect of IFN-γ on Protease HTRA1 Expression in Rheumatoid Arthritis, The Journal of Immunology, 2014, vol. 193, pp. 130-138.
Khan et al., Wogonin, a plant derived small molecule, exerts potent anti-inflammatory and chondroprotective effects through the activation of ROS/ERK/Nrf2 signaling pathways in human Osteoarthritis chondrocytes. Free Radical Biology and Medicine, Feb. 22, 2017, vol. 106, pp. 288-301.

(Continued)

*Primary Examiner* — Jared Barsky

(74) *Attorney, Agent, or Firm* — Barnes & Thornburg LLP; Ryan L. Marshall

(57) ABSTRACT

The invention described herein relates to compositions and methods for treating pain with wogonin. In particular, described herein are compositions and methods for treating musculoskeletal pain and arthritis with wogonin.

21 Claims, 9 Drawing Sheets
Specification includes a Sequence Listing.

(56) References Cited

OTHER PUBLICATIONS

Khan Nazir M. et al: "Wogonin. a natural flavonoid. intercalates with genomic DNA and exhibits protective effects in IL-1[beta] stimulated osteoarthritis chondrocytes", Chemico-Biological Interactions., vol. 274. Aug. 1, 2017 (Aug. 1, 2017). pp. 13-23. XP055858397, IR; ISSN: 0009-2797, DOI: 10.1016/j.cbi.2017.06.025.Park et al., Chondroprotective Effects of Wogonin in Experimental Models of Osteoarthritis in vitro and in vivo. Biomolecules and Therapeutics, 2015, vol. 23, No. 5, pp. 442-448.
Simonaro et al., Mechanism of Glycosaminoglycan-Mediated Bone and Joint Disease: Implications for the Mucopolysaccharidoses and Other Connective Tissue Diseases, Molecular Pathogenesis of Genetic and Inherited Diseases, 2008, vol. 172, No. 1, pp. 112-122.
Tang et al., Wogonoside inhibits IL-1β induced catabolismand hypertrophy in mouse chondrocyte and ameliorates murine osteoarthritis, Oncotarget, Jun. 6, 2017, vol. 8, No. 37, pp. 61440-61456.
The Journal of the Japanese Society of Internal Medicine, 2011, vol. 100, No. 10, pp. 2888-2901.
Yuan et al., Primary Cilia and Intraflagellar Transport Proteins in Bone and Cartilage, Clinical Reviews in Oral Biology and Medicine, 2016, vol. 95, No. 12, pp. 1341-1349.
Zhang et al., Bardet-Biedl syndrome 3 (Bbs3) knockout mouse model reveals common BBS-associated phenotypes and Bbs3 unique phenotypes, PNAS, Dec. 20, 2011, vol. 1 OB, No. 51, pp. 20678-20683; abstract.
Chen, Shibiao, et al.; "Wogonin inhibits LPS-induced inflammatory responses in rat dorsal root ganglion neurons via inhibiting TLR4-MyD88-TAK1-mediated NF-κB and MAPK signaling pathway"; Cell Mol Neurobiol; May 2015;35(4):523-31. doi: 10.1007/s10571-014-0148-4. Epub Dec. 14, 2014.
Wall, Patrick D., et al.; "Textbook of Pain"; Churchill Livingston; 1999. pp. 326-328.
Khan, Nazir M., et al.; "Dataset of effect of Wogonin, a natural flavonoid, on the viability and activation of NF-κB and MAPKs in IL-1β-stimulated human OA chondrocytes"; Data in Brief. Apr. 9, 2017;12:150-155. doi: 10.1016/j.dib.2017.03.054. eCollection Jun. 2017.
Non-Final Office Action for U.S. Appl. No. 16/961,186, dated Nov. 18, 2021, 8 pages.
Final Office Action for U.S. Appl. No. 16/961,186, dated Apr. 29, 2022, 8 pages.
Non-Final Office Action for U.S. Appl. No. 16/961,186, dated Nov. 8, 2022, 8 pages.
Final Office Action for U.S. Appl. No. 16/961,186, dated May 22, 2023, 9 pages.
Communication Under Rule 71(3) EPC for European Application No. 19738923.2, dated Jun. 21, 2023, 52 pages.
Decision to Grant for Japanese Application No. 2020-538049 with English translation, dated May 29, 2023, 6 pages.

* cited by examiner

TGF-β1 Stain Cell Count qRTPCR for TGF-β1 in Human Chondrocytes

```
                       SEQUENCE LISTING

Sequence total quantity: 4
SEQ ID NO: 1            moltype = DNA  length = 20
FEATURE                 Location/Qualifiers
misc_feature            1..20
                        note = TGF- beta 1 F primer
source                  1..20
                        mol_type = other DNA
                        organism = synthetic construct
SEQUENCE: 1
gcacgtggag ctgtaccaga                                                  20

SEQ ID NO: 2            moltype = DNA  length = 19
FEATURE                 Location/Qualifiers
misc_feature            1..19
                        note = TGF- beta 1 Reverse primer
source                  1..19
                        mol_type = other DNA
                        organism = synthetic construct
SEQUENCE: 2
gccggtagtg aacccgttg                                                   19

SEQ ID NO: 3            moltype = DNA  length = 21
FEATURE                 Location/Qualifiers
misc_feature            1..21
                        note = BBS 3 Forward primer
source                  1..21
                        mol_type = other DNA
                        organism = synthetic construct
SEQUENCE: 3
accagaaaaa ctgcctgctc t                                                21

SEQ ID NO: 4            moltype = DNA  length = 21
FEATURE                 Location/Qualifiers
misc_feature            1..21
                        note = BBS 3 Reverse primer
source                  1..21
                        mol_type = other DNA
                        organism = synthetic construct
SEQUENCE: 4
agcccaaggc acaaacatg a                                                 21
```

COMPOSITIONS AND METHODS FOR TREATING PAIN WITH WOGONIN

CROSS-REFERENCE TO RELATED APPLICATIONS

This application is a Continuation of U.S. application Ser. No. 16/961,186, filed Jul. 9, 2020, which is a 371 national phase of PCT/US2019/012869, filed Jan. 9, 2019, which claims the benefit of the filing date of U.S. Application No. 62/615,072, filed Jan. 9, 2018, and U.S. Application No. 62/756,188, filed Nov. 6, 2018, the disclosures of which are incorporated, in their entirety, by this reference.

SEQUENCE LISTING

The Sequence Listing associated with this application is provided in XML format in lieu of paper copy, and is hereby incorporated by reference into the specification. The name of the XML file containing the Sequence Listing is "82570-396649_SeqListing.xml". The XML file is 5.83 KB, was created on Oct. 18, 2023, and is being submitted electronically, concurrent with the filing of this specification.

TECHNICAL FIELD

The invention described herein relates to compositions and methods for treating pain with wogonin. In particular, described herein are compositions and methods for treating musculoskeletal pain and arthritis.

BACKGROUND INFORMATION

Musculoskeletal pain and arthritic pain is a major problem for people around the world. Pain stemming from these conditions is associated with aberrant inflammation. Particularly problematic is osteoarthritis (OA), which is a chronic disease affecting over 27 million people in the United States (U.S.) among many others. OA is recognized to be a multifactorial disease associated with risk factors such as obesity, joint-loading, acute injury, aging and joint-misalignment. As obesity rates increase and the mean age of the population advances, the incidence of OA is also increasing significantly.

Once thought to be a result of abnormal or excessive mechanical stress that physically degrades joint articular surfaces, recent research has increasingly shifted the understanding of OA from a disease of "wear and tear" to a metabolically active process involving both inflammatory and lipidomic biomarkers driving disease progression. Researchers have demonstrated the importance of cytokines such as HtrA1 and Mmp-13 in the progression of OA. As part of the inflammatory pathway driving OA progression, matrix degrading proteases HtrA1 and MMP-13 are secreted by chondrocytes into the pericellular and extracellular matrix, resulting in reduced matrix integrity and function.

In this context, researchers seek potent blocking of inflammation as potential therapeutic approaches to treating OA. For instance, words such as "potent and specific anti-cytokine treatments" or "blocking" of pro-inflammatory signaling have been used to describe the answer to treating OA (see, e.g., Kapoor M, et al., *Nature Reviews Rheumatology*. 2011; 7(1):33-42 and Kalaitzoglou E et al., *Curr Rheumatol Rep*. 2017; 19(8)).

To date, however, there are no successful treatment options that can reverse the disease etiology associated with OA. Thus, there is an unmet need for a safe and efficacious therapeutic that can both treat pain and the underlying disease mechanisms of OA while leading to joint regeneration and repair. In addition, there are limited options for the safe and effective treatment of conditions stemming from musculoskeletal pain.

BRIEF SUMMARY

The aforementioned limitations in treating pain including OA pain and musculoskeletal pain are addressed by the administration (e.g., topical administration) of low doses of wogonin or its derivatives thereof. Thus, some embodiments described herein are methods for reducing or relieving pain in a patient that includes locally administering a composition including wogonin or its derivatives thereof in a therapeutically effective amount of about 1 μM to about 500 μM locally to one or more sites of the patient having pain and reducing or relieve the pain. In some embodiments, the pain is selected from a musculoskeletal pain and arthritis pain. In some embodiments, musculoskeletal pains to be treated stem from a sore muscle, a strained muscle, a bruised muscle, or a torn muscle. In other embodiments, the musculoskeletal pain stems from a sore tendon, a strained tendon, a bruised tendon, or a torn tendon. In some embodiments, arthritis pain includes osteoarthritis pain and rheumatoid arthritis pain. In some embodiments, a perception of the pain by the patient is reduced by about 10% to about 100% after administration of the wogonin.

In some embodiments, the topical administration for reducing or relieving pain is transdermal administration. In some embodiments, a single dose of wogonin is $3.73 \times 10^{-9}$ g/Kg to about $1.87 \times 10^{-6}$ g/Kg and a daily dose of wogonin is $1.12 \times 10^{-8}$ g/Kg to about $5.61 \times 10^{-6}$ g/Kg per day. In some embodiments, wogonin is administered as an immediate release topical formulation, a delayed release topical formulation, a continuous release topical formulation, or an extended release topical formulation. In some embodiments one or more additional anti-inflammatory drugs are administered before, after, or concurrently with the local administration of wogonin.

In some embodiments, compositions for treating or reducing pain with wogonin includes a concentration of wogonin selected from about 1 μM, 5 μM, 10 μM, 20 μM, 40 μM, 60 μM, 80 μM, 100 μM, 120 μM, 140 μM, 160 μM, 180 μM, 200 μM, 220 μM, 240 μM, 260 μM, 280 μM, 300 μM, 320 μM, 340 μM, 360 μM, 380 μM, 400 μM, 420 μM, 440 μM, 460 μM, 480 μM, and 500 μM of wogonin. In some embodiments, the composition is in a form of a liquid, rub, foam, cream, solution, emulsion, gel, spray, wipes, a lotion, or a patch or combinations thereof. In some embodiments, the composition is a cream, wherein the cream includes one or more transdermal penetration enhancers.

Some embodiments described herein are methods for treating and promoting healing of an arthritic joint in a patient including topically administering a composition that includes wogonin in a therapeutically effective amount of about 1 μM to about 500 μM locally to one or more arthritic joints of the patient, thereby treating and promoting the healing of the arthritic joint. In some embodiments, the administration of wogonin reduces inflammation within the arthritic joint. In some embodiments, the therapeutically effective amount elicits an effect comprising decreased cyst-like lesions (CLLs), a lower OARSI score, and inhibition of the primary cilia pathway of cartilage degradation.

In some embodiments following the administration of wogonin an expression of a ceramide is increased, TGF-β1 is increased, MMP-13 is decreased, HtrA1 is decreased, NFκB is decreased, and AGE is decreased within or proximally surrounding the arthritic joint, including cartilage and synovial fluid, compared to an arthritic joint not treated with wogonin. In some embodiments following the administration of wogonin an expression of cytokines HtrA1, MMP-13, NFκB and AGE are reduced by 20% and TGF-β1 and ceramide are elevated by 20% compared to an arthritic joint not treated with wogonin. In some embodiments, the arthritic joint is an osteoarthritic joint.

Some other embodiments are topical pain compositions that include a concentration of wogonin of about 1 μM to about 500 μM and a cosmetically or dermatologically acceptable carrier. In some embodiments, the wogonin is about 90% to about 100% pure. In some embodiments, the topical pain compositions are in a form of a liquid, a rub, a foam, a cream, a solution, an emulsion, a gel, a spray, wipes, a lotion, or a patch or combinations thereof. In some embodiments, the topical pain composition includes one or more excipients selected from a surfactant, an emulsifier, a fat, a fatty acid, a triglyceride, a solvent, a thickener, a skin conditioning agent, a chelator, a fragrance, a penetration enhancer, and combinations thereof.

In some embodiments, the carrier in the topical pain composition includes one or more excipients selected from cetearyl alcohol, caprylic/capric triglyceride, glycerin, shea butter, ethoxydiglycol, glyceryl stearate, peg-100 stearate, stearic acid, butylene glycol, dimethicone, mentha piperita (peppermint) oil, coconut oil, polyethylene glycol, prunus amygdalus dulcis (sweet almond) oil, hydroxyethyl acrylate/, sodium acryloyldimethyl taurate copolymer, ceteareth-20, dimethyl sulfone, squalane, phenoxyethanol, caprylyl glycol, acrylates/c10-30 alkyl acrylate crosspolymer, xanthan gum, ethylhexylglycerin, hexylene glycol, tetrasodium glutamate diacetate, polysorbate 60, sorbitan isostearate, aloe barbadensis leaf juice, and menthol and combinations thereof.

In some embodiments, the composition described herein comprise dimethyl sulfone, polyethylene glycol or polypropylene glycol, peppermint oil, coconut oil, and shea butter. In some embodiments, the composition described herein comprises: a). about 0.03% to about 5% dimethyl sulfone; b). about 1% to about 8% polyethylene glycol or polypropylene glycol; c). about 1% to about 7% peppermint oil; d). about 0.3% to about 50% shea butter; e). about 0.14% to about 26% coconut oil; and f). about 15% to about 85% water.

DETAILED DESCRIPTION

Figure 1:
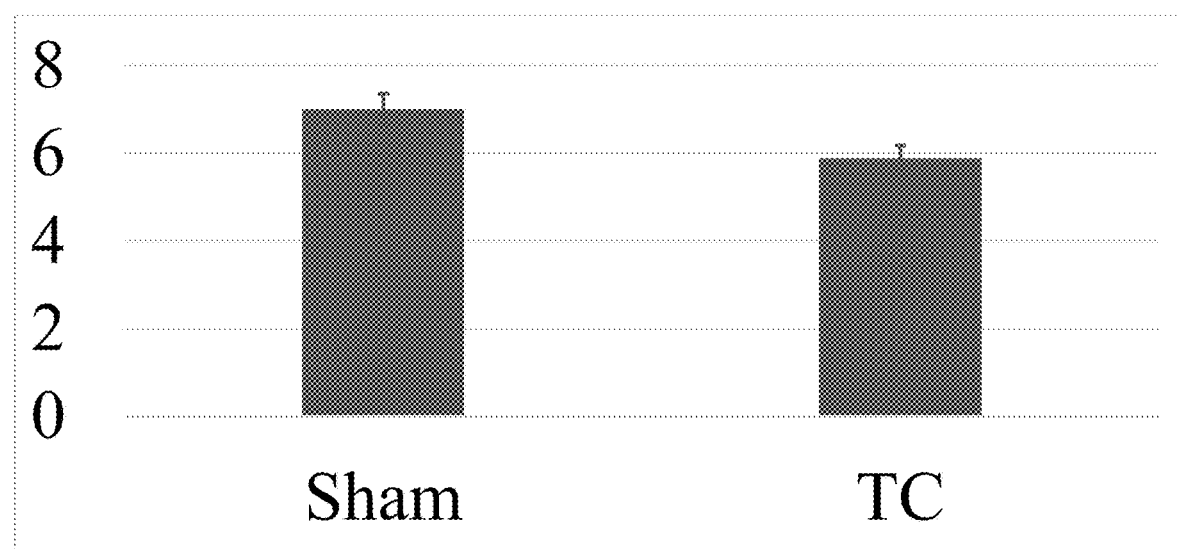
FIG. 1 is a bar graph comparing the modified Mankin score of mice treated with 10 μM wogonin or vehicle after receiving DMM knee destabilization surgery (*p>0.05)

The following description defines in more detail the embodiments of the invention described herein. The following embodiments are not meant to limit the invention or narrow the scope thereof, as it will be readily apparent to one of ordinary skill in the art that suitable modifications and adaptations may be made without departing from the scope of the invention, embodiments, or specific aspects described herein. All patents and publications cited herein are incorporated by reference herein in their entirety.

For purposes of interpreting this specification, the following terms and definitions will apply and whenever appropriate, terms used in the singular will also include the plural and vice versa. In the event that any definition set forth below conflicts with any document incorporated herein by reference, the definition set forth below shall control.

The term "patient" refers to any subject including mammals and humans. The patient may have a disease or suspected of having a disease and as such is being treated with a drug. In some instances, the patient is a mammal, such as a dog, chicken, cat, horse, or primate. In some instances, the term "patient," as used herein, refers to a human (e.g., a man, a woman, or a child). In some instances, the term "patient," as used herein, refers to laboratory animal of an animal model study. The patient or subject may be of any age, sex, or combination thereof.

The terms "active ingredient," "active pharmaceutical ingredient," "bioactive agent," or "therapeutic agent" as used herein refer to a pharmaceutical agent, active ingredient, compound, substance or drug, compositions, or mixtures thereof, that provide a pharmacological, often beneficial, effect. The active ingredient may be any pharmaceutically acceptable salt, hydrate, crystalline form or polymorph thereof.

The term "alkyl" as used herein alone or as part of another group, refers to a straight or branched chain hydrocarbon containing from one or more carbon atoms. In some embodiments, alkyl represents between 1 and 4 carbon atoms. Representative examples of alkyl include, but are not limited to, methyl, ethyl, n-propyl, iso-propyl, n-butyl, sec-butyl, iso-butyl, and tert-butyl. In some embodiments, alkyl may be straight chained. In some embodiments, alkyl may be branched.

The term "alkoxy" as used herein alone or as part of another group, refers to an alkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, hexyloxy and the like.

The term "halo" or "halogen" as used herein refers to any suitable halogen, including —F, —Cl, —Br, and —I.

The terms "isolated" and "purified" as used herein are used interchangeably and refer to a compound or compositions including the compound that is at least about 30%, 40%, 50%, 60%, 70%, 80%, 90%. 95%, 99%, or 100% by weight, free from proteins and naturally-occurring organic molecules with which the compound is naturally associated. In some embodiments described herein, wogonin is purified or isolated by any method known in the art or described herein including, for example, high pressure liquid chromatography, thin layer chromatography, or by synthesis.

The term "formulation" or "composition" as used herein refers to the active ingredient or drug in combination with pharmaceutically acceptable excipients.

The terms "dosage" or "dose" as used herein denote any form of the active ingredient formulation that contains an amount sufficient to produce a therapeutic effect with a single administration.

The term "modified release" as used herein refers to a composition that releases an active ingredient at a slower rate than does an immediate release formulation under physiological conditions or in an in vitro test.

The term "immediate release" as used herein refers to a composition that releases the majority of an active ingredient following administration (e.g., greater than 50% of the active ingredient).

The term "sustained release" as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "delayed release" as used herein refers to a composition that releases an active ingredient according to a desired profile after a delayed time period. The delayed time period may be after a period of time from the administration of the composition of at least about 5 minutes, 10 minutes, 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer. After the delayed time period, the composition may be immediately released or released following a sustained or extended release profile.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer.

The term "treating" refers to administering a therapy in an amount, manner, or mode effective to improve a condition, symptom, or parameter associated with a disorder. In some embodiments, treating refers to the amelioration of pain stemming from arthritis (e.g., osteoarthritis) or a musculoskeletal pain. In some embodiments, treating refers to the reversal of a disease process, such as arthritis (e.g., osteoarthritis) and permanent healing.

The term "local administration" or "localized administration" refers to the administration of a therapeutic agent (i.e., wogonin) to one or more tissues having OA, OA pain, or musculoskeletal pain. The local administration means that the therapeutic agent is administered in proximity to the afflicted tissue without being administered systemically. Following administration locally, it is contemplated that the active agent can be absorbed by the lymphatic or vascular system and subsequently cleared from the tissue. However, the mechanism of action is believed to predominantly occur by the local interaction of the therapeutic agent with the afflicted tissue.

The term "prophylaxis" refers to preventing or reducing the progression of a disorder, either to a statistically significant degree or to a degree detectable to one skilled in the art.

As used herein, "a" or "an" means one or more unless otherwise specified.

As described herein, the inventors discovered a surprisingly effective approach to treating OA and musculoskeletal pain with low doses of wogonin applied topically, which in some embodiments is from about 1 µM to about 500 µM. It was also discovered that topical administration of wogonin restores joint homeostasis and abrogates progression of OA disease processes. In addition, the inventors found that topical administration of wogonin reverses chondrocyte activation that results in apoptosis in affected cartilage thereby promoting damaged joint cartilage healing.

These substantial effects from topical administration of wogonin have never before been realized. Wogonin is a flavonoid derived from the root of *Scutellaria baicalensis*, which is a traditional Chinese herbal remedy. It has been used for the treatment of inflammatory diseases, including atopic dermatitis, hyperlipidemia, and atherosclerosis. More recently, wogonin has been investigated for its use in other inflammatory diseases, cancer, and pain management through blocking prostaglandin E2, TLR4, NO, and MMP production, which can decrease inflammation. For example, U.S. Patent Application Publication No. 2013/0136811 described the improvement of pain symptoms in a mouse formalin test following the systemic application via intraperitoneal injection of large doses of wogonin (i.e., 200 mg/kg). This approach, however, did not determine whether the topical and local administration of wogonin at low doses could reduce pain stemming from OA or musculoskeletal pain. This study also did not indicate whether wogonin could have any effect on restoring joint homeostasis reversing OA disease progression. Another study described by Park et al., *Biomolecules & Therapeutics*. 23(5) pp. 442-448 (2015) assessed the effects of intra-articular injection of wogonin on MMP-3 expression in articular cartilage following initiation of inflammation by IL-1β, which may be involved in the disease progression of OA. While the authors demonstrated decreased MMP-3 expression, this study did not determine whether the topical administration of low doses of wogonin could ameliorate pain stemming from osteoarthritis or musculoskeletal pain or lead to functional recovery of an osteoarthritic synovial joint.

In contrast thereto, the methods and compositions described herein go against conventional expectations that using very potent anti-inflammatory drugs and other approaches for treating OA applied systemically or by injection. As demonstrated herein, utilizing low-doses of topical wogonin can accelerate joint repair and healing where the wogonin optimally modulates inflammation enhancing natural protective mechanisms to aid in the healing process. Thus, treating the inflammatory component of OA is like walking a razors edge—too little and no effect, too much and OA is worsened. In addition, treating inflammation alone is also insufficient. It is also necessary for the chondrocyte to switch from an apoptotic pathway to autophagy, such that it can continue to produce proteoglycan, collagen fibrils etc. leading to healing of the joints. Thus, the methods and compositions described herein are suitable for the treatment of all types of osteoarthritis. In addition, it is contemplated that other types of arthritis including rheumatoid arthritis pain can be ameliorated by the administration of low doses of wogonin.

As described herein, the inventors discovered that the disclosed compositions exhibit a protective effect through a novel interaction with primary cilia. Primary cilia exist on chondrocytes, and primary cilia in mouse chondrocytes are associated with signal processing in response to increased loads. Primary cilia are associated with cartilage homeostasis, including OA through up-regulation of the previously identified HTRA1-DDR2-MMP13 degradative pathway common to OA.

Further evidence exists of the role of primary cilia in OA progression such as the involvement of Hes1 in upregulating MMP-13 expression. Hes1 acts through the Notch signaling pathway modulating sonic hedgehog signaling through primary cilia.

The role of inflammation in OA has been clearly shown, yet the use of powerful anti-inflammatory agents has not stopped the progression of the disease. The disease appears to be more complex than simple inflammation. For instance, the interaction of adipokines, such as the peptide hormone leptin, and inflammation in initiating OA is known. Leptin, involved in maintaining insulin sensitivity, expressed at high levels in obese individuals is correlated with osteoarthritis by upregulating MMP-13 expression in chondrocytes. In cases of extreme obesity, a strong positive correlation exists between the upregulation of MMP-13 and leptin expression with the BMI of osteoarthritic individuals. Primary cilia are intimately involved in leptin homeostasis. Additionally, the nuclear factor kappa beta (NFκβ pathway has been shown to be intimately associated with OA progression. NFκβ is known to be regulated by primary cilia.

Primary cilia are intimately involved in maintaining cartilage homeostasis and that treatment of OA must take that into account and not rely solely on blocking inflammation. Herein, the inventors demonstrate that wogonin compositions exhibit protective effects on chondrocytes holistically by acting through primary cilia and that topical application of wogonin attenuates OA progression, thereby treating the disease. This is a novel pathway not previously attributed to wogonin and explains why it has a powerful holistic benefit to an osteoarthritic joint when applied topically (e.g., as a cream).

As demonstrated herein, wogonin applied in a topical, transdermal cream is useful for abrogating the progression of OA. Wogonin applied according to the methods and in the compositions described herein blocks the progression of OA in mice in which the OA disease is induced by knee destabilization surgery. As described herein, joint health is restored, as evidenced by several key indicators. Furthermore, the use of wogonin according to the methods and compositions described herein restores joint health after disease is induced and allowed to progress before treatment. Anti-inflammatories have been used for many years to treat the symptoms (i.e. pain) of OA, without blocking the progression of the disease, let alone restoring the joint health. The data provided herewith indicates that topical, transdermal treatment leads to a switch from apoptosis to autophagy in stressed chondrocytes and restores joint health—a process for treating the underlying disease pathology of OA.

The advantages of the disclosed methods and compositions are two-fold. First, the methods and compositions provide a site-specific (i.e. joint) treatment for OA. Second, it treats physiologic consequences of chondrocyte activation associated with OA. In addition, the disclosed treatment with wogonin limits or obviates the use of non-steroidal anti-inflammatory drugs and opiates, which work systemically and have deleterious side effects such as addition or damage to internal organs.

Furthermore, the methods and compositions described herein are suitable for local administration and relief of other non-arthritic inflammatory musculoskeletal pains stemming from sore strained, bruised muscle, or torn muscles. Likewise, the methods and compositions described herein are suitable for local administration and relief of pain stemming from sore, strained, bruised, or torn tendons.

Some embodiments described herein relate to the use of the compound wogonin or its derivatives thereof for the treatment of pain. In particular, described herein is the use of wogonin or its derivatives thereof for the treatment of OA, OA pain, and musculoskeletal pain. Exemplary derivatives of wogonin are known (see e.g., Gurung S K, and Kim H P, Park H. *Arch Pharm Res*. Nov 32(11) pp. 1503-8 (2009) and are according to Formula I.

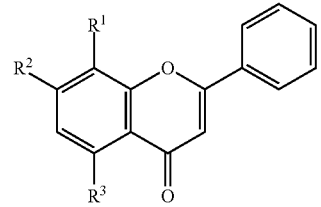

Formula I wherein $R^1$, $R^2$, and $R^3$ are each independently selected from —H, -halo, —OH, $C_1$-$C_4$ alkyl, $C_1$-$C_4$ alkoxy, —$NO_2$, and —SX, wherein X is $C_1$-$C_4$ alkyl.

In some embodiments, the methods and compositions described herein relate to the use of wogonin (5,7-dihydroxy-8-methoxyflavone; CAS Registry Number 632-85-9) (displayed below as Formula II) for the treatment of pain. In particular, described herein is the use of wogonin according to Formula II for the treatment of OA, OA pain, and musculoskeletal pain.

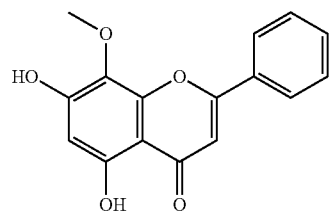

Formula II

Some embodiments described herein are methods for reducing or relieving pain stemming from OA in a patient including administering a composition including wogonin in a therapeutically effective amount. Synovial joints affected by OA that are suitable for treatment with wogonin include one or more joints of the spine, upper limbs, elbows, head, neck, thorax, pelvis, perineum, or lower limb joints. Thus, the synovial joint to be treated includes a zygapophyseal joint, acromioclav-icular joint, finger carpometacarpal joint, thumb carpometacarpal joint, coracoclav-icular joint, elbow joint, intermetacarpal joint, interphalangeal joint, metacarpo-phalangeal joint, midcarpal joint, wrist radiocarpal, distal radioulnar joint, inter-mediate radioulnar joint, proximal radioulnar joint, shoulder joint, sternoclavicular joint, wrist joint, temporomandibular joint, sternocostal joint, xiphisternal joint, lumbo-sacral joint, sacroiliac joint, ankle joint, hip joint, interphalangeal joint, or knee joint.

In some embodiments, wogonin is administered following a surgery involving the one or more synovial joints that is susceptible to developing OA. Wogonin can be administered prior to, at the same time, or after a surgery involving the one or more synovial joints. Types of joint surgeries include but are not limited to arthroplasty, arthroscopic surgery, osteotomy, synovectomy, joint replacement, or laminectomy or a combination thereof.

In some embodiments, the administration of wogonin is a topical administration having an effective amount to reduce or eliminate a musculoskeletal pain or an OA pain. This amount of wogonin is also effective to promote healing of joints having OA. In one embodiment, the amount of wogonin is about 1 µM to about 500 µM, including each integer within the recited range. In another embodiment, the amount of wogonin is about 1 µM to about 400 µM, about 1 µM to about 300 µM, about 1 µM to about 200 µM, about 1 µM to about 10 µM, or about 1 µM to about 50 µM including each integer within the recited ranges. In another embodiment, the amount of wogonin is about 10 µM to about 500 µM, about 10 µM to about 400 µM, about 10 µM to about 300 µM, about 10 µM to about 200 µM, about 10 µM to about 100, or about 10 µM to about 50 µM including each integer within the recited ranges. In another embodiment, the amount of wogonin is about 1 µM, 5 µM, 10 µM, 20 µM, 40 µM, 60 µM, 80 µM, 100 µM, 120 µM, 140 µM, 160 µM, 180 µM, 200 µM, 220 µM, 240 µM, 260 µM, 280 µM, 300 µM, 320 µM, 340 µM, 360 µM, 380 µM, 400 µM, 420 µM, 440 µM, 460 µM, 480 µM or about 500 µM.

In some embodiments, wogonin is administered as a single dose that is therapeutically effective to reduce pain stemming from OA or a musculoskeletal pain. In one embodiment, the dose is about $3.73 \times 10^{-9}$ g/Kg to about $1.87 \times 10^{-6}$ g/Kg, including each integer within the specified range. In another embodiment, the dose is about $3.73 \times 10^{-9}$ g/Kg to about $1.49 \times 10^{-6}$ g/Kg, including each integer within the specified range. In another embodiment, the dose is about $3.73 \times 10^{-9}$ g/Kg to about $1.12 \times 10^{-6}$ g/Kg, including each integer within the specified range. In another embodiment, the dose is about $3.73 \times 10^{-9}$ g/Kg to about $7.5 \times 10^{-7}$ g/Kg, including each integer within the specified range. In another embodiment, the dose is about $3.73 \times 10^{-9}$ g/Kg to about $4.48 \times 10^{-7}$ g/Kg, including each integer within the specified range. In another embodiment, the dose is about $3.73 \times 10^{-9}$ g/Kg to about $2.24 \times 10^{-7}$ g/Kg, including each integer within the specified range. In another embodiment, the dose is about $3.73 \times 10^{-9}$ g/Kg, $1.87 \times 10^{-8}$ g/Kg, $3.73 \times 10^{-8}$ g/Kg, $7.47 \times 10^{-8}$ g/Kg, $1.49 \times 10^{-7}$ g/Kg, $2.24 \times 10^{-7}$ g/Kg, $2.99 \times 10^{-7}$ g/Kg, $3.73 \times 10^{-7}$ g/Kg, $4.48 \times 10^{-7}$ g/Kg, $5.23 \times 10^{-7}$ g/Kg, $5.97 \times 10^{-7}$ g/Kg, $6.72 \times 10^{-7}$ g/Kg, $7.5 \times 10^{-7}$ g/Kg, $8.2 \times 10^{-7}$ g/Kg, $8.96 \times 10^{-7}$ g/Kg, $9.71 \times 10^{-7}$ g/Kg, $1.05 \times 10^{-6}$ g/Kg, $1.12 \times 10^{-6}$ g/Kg, $1.19 \times 10^{-6}$ g/Kg, $1.27 \times 10^{-6}$ g/Kg, $1.34 \times 10^{-6}$ g/Kg, $1.42 \times 10^{-6}$ g/Kg, $1.49 \times 10^{-6}$ g/Kg, $1.57 \times 10^{-6}$ g/Kg, $1.64 \times 10^{-6}$ g/Kg, $1.72 \times 10^{-6}$ g/Kg, $1.79 \times 10^{-6}$ g/Kg, or $1.87 \times 10^{-6}$ g/Kg.

In some embodiments, the total dose of wogonin per day is about $1.12 \times 10^{-8}$ g/kg to about $5.61 \times 10^{-6}$ g/kg per day. In another embodiment, the dose is about $1.12 \times 10^{-8}$ g/Kg to about $4.47 \times 10^{-6}$ g/Kg, including each integer within the specified range. In another embodiment, the dose is about $1.12 \times 10^{-8}$ to about $3.36 \times 10^{-6}$ g/Kg, including each integer within the specified range. In another embodiment, the dose is about $1.12 \times 10^{-8}$ to about $2.3 \times 10^{-6}$ g/Kg, including each integer within the specified range. In another embodiment, the dose is about $1.12 \times 10^{-8}$ to about $1.34 \times 10^{-6}$ g/Kg, including each integer within the specified range. In another embodiment, the dose is about $1.12 \times 10^{-8}$ g/Kg to about $6.72 \times 10^{-7}$ g/Kg, including each integer within the specified range. In another embodiment, the dose is about $1.12 \times 10^{-8}$ g/Kg, $5.61 \times 10^{-8}$ g/Kg, $1.12 \times 10^{-7}$ g/Kg, $2.2 \times 10^{-7}$ g/Kg, $4.47 \times 10^{-7}$ g/Kg, $6.72 \times 10^{-7}$ g/Kg, $8.97 \times 10^{-7}$ g/Kg, $1.12 \times 10^{-6}$ g/Kg, $1.34 \times 10^{-6}$ g/Kg, $1.57 \times 10^{-6}$ g/Kg, $1.8 \times 10^{-6}$ g/Kg, $2.0 \times 10^{-6}$ g/Kg, $2.3 \times 10^{-6}$ g/Kg, $2.5 \times 10^{-6}$ g/Kg, $2.7 \times 10^{-6}$ g/Kg, $2.9 \times 10^{-6}$ g/Kg, $3.1 \times 10^{-6}$ g/Kg, $3.4 \times 10^{-6}$ g/Kg, $3.6 \times 10^{-6}$ g/Kg, $3.8 \times 10^{-6}$ g/Kg, $4.0 \times 10^{-6}$ g/Kg, $4.3 \times 10^{-6}$ g/Kg, $4.5 \times 10^{-6}$ g/Kg, $4.7 \times 10^{-6}$ g/Kg, $4.9 \times 10^{-6}$ g/Kg, $5.1 \times 10^{-6}$ g/Kg, $5.3 \times 10^{-6}$ g/Kg, or $5.6 \times 10^{-6}$ g/Kg.

In some embodiments, the administration of wogonin modulates the expression of one or more inflammatory biomarker genes including but not limited to a ceramide, TGF-β1, MMP-13, HtrA1, NFκB, and AGE. In some embodiments, the expression of TGF-β1 in a tissue in which the wogonin is administered is upregulated by about 10% to about 40% compared to a tissue not treated with wogonin, including each integer within the specified range. In some embodiments, the expression of ceramide in a tissue in which the wogonin is administered is upregulated by about 10% to about 40% compared to a tissue not treated with wogonin including each integer within the specified range. In some embodiments, the expression of MMP-13 in a tissue in which the wogonin is administered is upregulated by about 10% to about 40% compared to a tissue not treated with wogonin, including each integer within the specified range. In some embodiments, the expression of NFκB in a tissue in which the wogonin is administered is downregulated by about 10% to about 40% compared to a tissue not treated with wogonin, including each integer within the specified range. In some embodiments, the expression of AGE in a tissue in which the wogonin is administered is downregulated by about 10% to about 40% compared to a tissue not treated with wogonin, including each integer within the specified range. The determination of expression of gene levels is well known in the art. For example, the levels of a gene expression can be determined by real time polymerase chain reaction (RT-PCR), Western blotting, immunohistochemistry, and the like.

In some embodiments, a perception of pain in one or more tissues having a pain is reduced following administration of wogonin to the tissue. In some embodiments, following the administration of wogonin, the perception of pain is reduced by at least about 10%, 20%, 30%, 40%, 50%, 60%, 70%, 80%, 90%, 95% or even 100%. In some embodiments, the reduction in pain is in a musculoskeletal tissue. In some other embodiments, the reduction in pain is in a joint having arthritic pain stemming from OA. In some other embodiments, the reduction in pain is in a joint having arthritic pain stemming from rheumatoid arthritis. Methods for assessing pain are known in the art. For example, the McGill pain Questionnaire (MPQ), the Intermittent and Constant Osteoarthritis (ICOAP) questionnaire, or the Osteo-Arthritis Symptom Inventory Scale (OASIS) can be used to assess pain in patients having osteoarthritis.

In addition, the Osteoarthritis Society International (OARSI) scale represents a holistic procedure for assessing OA progression and joint health, which may be used to assess OA disease in the methods described herein. A reduction in OARSI score is indicative of an improvement in joint health and reduction in OA disease. Accordingly, in some embodiments, following administration of wogonin, the OARSI score is reduced by at least 10%, 20%, 30%, 40%, 50%, 60%, 70%, 80%, or 90%. In some embodiments, the OARSI score is reduced by an amount, which is representative of a completely healed joint or of a joint that does not have osteoarthritis.

In some embodiments, the effective dose is administered one or more times per day to the site of a patient having pain. The dosage can be administered, for example, 1×, 2×, 3×, 4×, 5×, 6×, or even more times per day. In some embodiments, the dosage is administered at least 3 times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months (1 year), 2 years, 3 years, 4 years, 5 years, over 5 years, a decade, multiple decades, or even longer. One or more dosage forms can be administered at a regular interval until the subject or subject in need thereof, does not require treatment for pain.

In some embodiments, wogonin is isolated and purified, such that the compound is substantially free of any other components that are naturally associated with the wogonin. In some embodiments, the wogonin is at least about 20% pure, 30% pure, 40% pure, 50% pure, 60% pure, 70% pure, 80% pure, 90% pure, 95% pure, 99% pure, or 100% pure. In some embodiments, the wogonin is synthesized such that the wogonin is at least about 20% pure, 30% pure, 40% pure, 50% pure, 60% pure, 70% pure, 80% pure, 90% pure, 95% pure, 99% pure, or 100% pure. The isolation and purification of wogonin can be carried out by methods known in the art (see e.g., U.S. Patent Publication No. 2013/013681) or may be prepared synthetically and is also available commercially from Sigma-Aldrich (St. Louis, MO, USA).

In some embodiments, wogonin is administered as part of a composition. In some embodiments, the composition is formulated for a topical administration, transdermal administration, subcutaneous administration or a local injection. In particular, the compositions described herein are formulated for transdermal administration. Without being bound by any theory, once the transdermal composition including wogonin is applied, it is thought that wogonin is able to pass through the stratum corneum of the epidermis and into the deeper tissue layers of the epidermis, dermis, and subcutaneous tissue layers, where it can exert localized antinociceptive, anti-inflammatory, and joint healing effects.

In some embodiments, the wogonin is administered topically to one or more tissues. In some embodiments, the tissue is a musculoskeletal tissue. In some embodiments, the tissue overlays one or more synovial joints that is exhibiting or susceptible to OA pain. The wogonin remains at the local site of administration for a period of time, for example for at least about 30 minutes to 8 hours or more, exhibiting a localized reduction in pain in the tissue having pain.

In some embodiments, the transdermal composition including wogonin is provided as part a liquid, rub, foam, cream, solution, emulsion, gel, spray, wipes, a lotion, ointment, or a patch. In some embodiments, the transdermal formulation including wogonin or its derivatives is a cream, lotion, ointment or rub.

Suitable topical transdermal compositions, such as a cream or rub include a cosmetically or dermatologically acceptable excipients and carriers. The wogonin may be dispersed, dissolved, or suspended in the composition. Suitable excipients and carriers include but are not limited to one or more of an oil, a surfactant, an emulsifier, thickening agents, fragrances, solvents, chelators, and penetration promoters as known in the art.

Suitable penetration promoters are those, which can penetrate into the skin and interact with the constituents of the stratum corneum, which is the main impediment to penetration of the active substance. Penetration promoters reduce the resistance of the skin and thus increase the passage (flux) of the active substance through the skin. In most cases, they also beneficially affect the active substance partition ratio between skin and vehicle. Exemplary and non-limiting penetration promoters include dioxolane derivatives, ethyl acetate, urea, ethanol, short-chain monohydric alcohols ($C_2$-$C_6$), propylene glycol, ethanol, DMSO, DMF, laurocapram and derivatives, fatty acids (e.g., oleic acid), surfactants (e.g., decyl methyl sulphoxide), terpenes, isopropanol, glycerol, monohydric alcohols ($C_8$-$C_{14}$), alkanes, alkyl halides, amides, pyrrolidone derivatives, fatty acid esters, cyclodextrins, polyethylene glycols, essential oils, such as peppermint oil and other penetration enhancers known in the art (see e.g., Herman, A and Herman A. P., *Journal of Pharmacy and Pharmacology.*, 67, pp. 473-485 (2014)).

In some embodiments, transdermal compositions including wogonin are formulated as a modified release transdermal formulation, an immediate release transdermal formulation, a delayed release transdermal formulation, a sustained release transdermal formulation, or an extended release transdermal formulation. Exemplary and nonlimiting formulations suitable for transdermal administration of compounds are described in U.S. Pat. Nos. 6,238,284; 5,725,876; 5,716,635; 5,633,008; 5,603,947; 5,422,361 5,411,739; 5,364,630; 5,230,896; 5,004,610; 4,943,435; 4,908,213; and 4,839,174. An exemplary transdermal cream composition is provided in Table 1.

TABLE 1

Exemplary Cream Composition

| Ingredients | Percent by weight |
| --- | --- |
| Surfactant (e.g., peg-stearate) | 0% or 0.1-3% |
| Emulsifier (e.g., glyceryl stearate) | 0% or 0.01-3% |
| Fat, fatty acid or triglyceride (e.g., shea butter, stearic acid, glyceryl stearate) | 0% or 0.1-51% |
| Solvents (e.g., dimethyl sulfone; ethoxydiglycol; polyethylene glycol) | 0% or 0.1-10% |
| Thickener (e.g., acrylates/C10-C30 alkyl acrylate crosspolymer; xanthan gum) | 0% or 0.01-6% |
| Skin conditioning agent (e.g., caprylic/capric triglyceride; menthol) | 0% or 0.01-5% |
| Chelators (e.g., tetrasodium glutamate diacetate; ethylenediaminetetraacetic acid) | 0% or 0.001-3% |
| Fragrances (e.g., coconut oil; prunus amygdalus dulcis (sweet almond) oil) | 0% or 0.01-3% |
| Penetration enhancer (e.g., peppermint oil, propylene glycol, DMSO, oleic acid, 1-dodecylazacycloheptan-2-one, N-(4-bromobenzoyl)-S,S-dimethyllimino-sulfurane, methylsulfonylmethane, iminosulfurane, dimethyl sulfone) | 0.1-15% |
| Water | 0-90% |
| Wogonin | 0.00003-1% |

In some embodiments, the composition for topical and transdermal administration includes one or more or all of the following excipients or carriers: cetearyl alcohol, caprylic/ capric triglyceride, glycerin, shea butter, ethoxydiglycol, glyceryl stearate, peg-100 stearate, stearic acid, butylene glycol, dimethicone, mentha piperita (peppermint) oil, coconut oil, polyethylene glycol, prunus amygdalus dulcis (sweet almond) oil , hydroxyethyl acrylate/, sodium acryloyldimethyl taurate copolymer, ceteareth-20, dimethyl sulfone, squalane, phenoxyethanol, caprylyl glycol, acrylates/$C_{10}$-$C_{30}$ alkyl acrylate crosspolymer, xanthan gum, ethylhexylglycerin, hexylene glycol, tetrasodium glutamate diacetate, polysorbate 60, sorbitan isostearate, aloe barbadensis leaf juice, or menthol.

In some embodiments, the composition is a roll-on topical formulation. In some embodiments, the composition includes one or more or all of the following excipients or carriers: water, alcohol, caprylic/capric triglyceride, propanediol, ethoxydiglycol, mentha piperita (peppermint) oil, dimethicone, cetearyl alcohol, glyceryl stearate, potassium olivoyl hydrolized oat protein, cetyl alcohol, xanthan gum, phenoxyethanol, caprylyl glycol, glyceryl oleate, sclerotium gum, lecithin, ethylhexylglycerin, hexylene glycol, pullulan, menthol, and sodium phytate.

The application of the transdermal composition can be anywhere on the skin having a close proximity to the perceived pain. For example, for treating musculoskeletal pain, a transdermal cream having wogonin can be applied on the skin that lies above the afflicted tissue where pain is perceived. As an additional example, for treating arthritic pain stemming from the knee, a transdermal cream having wogonin can be applied on the skin surrounding the knee. The application of transdermal and topical creams for the treatment of pain and inflammation is appreciated in the art and placement of the cream can be adapted based upon the pain type.

In some embodiments, the composition including wogonin is formulated for a local injection. The local injection includes any injection, which provides the composition including wogonin in proximity to a tissue that exhibits or is susceptible to pain. For example, for treating a musculoskeletal pain, a composition including wogonin can be injected near where the pain is being perceived. As an additional example, the treatment of an arthritic joint may be accomplished by intraarticular injection of the composition including wogonin to the joint. Methods and devices for injection, including intraarticular injection are well known to a person having skill in the art. Exemplary injectable compositions for the local injection of wogonin include physiologically compatible aqueous solutions, such as Hanks's solution, Ringer's solution, or 415 physiological saline buffer.

Other compositions for other parenteral administration include aqueous solutions of the compounds of the invention in water-soluble form. Additionally, suspensions of wogonin can be prepared as appropriate oily-injection suspensions. Suitable lipophilic solvents or vehicles include fatty oils, such as sesame oil, or synthetic-fatty-acid esters, such as ethyl oleate or triglycerides, or liposomes. Aqueous-injection suspensions contain substances that increase the viscosity of the suspension, such as sodium carboxymethyl cellulose, sorbitol, or dextran. Optionally, the suspension contains suitable stabilizers or agents that increase the solubility of the compounds of the invention to allow for the preparation of highly concentrated solutions.

The purified wogonin can be formulated for parenteral administration by injection, e.g., by bolus injection or continuous infusion. Formulations for injection are presented in unit-dosage form, e.g., in ampules or in multi-dose containers, optionally with an added preservative. The compositions take such forms as suspensions, solutions, or emulsions in oily or aqueous vehicles, and contain formulatory agents, such as suspending, stabilizing, or dispersing agents. Alternatively, the compounds or extract is in powder form for constitution with a suitable vehicle, e.g., sterile pyrogen-free water, before use. An injectable formulation containing wogonin may be provided in the form of a portable kit or package.

The amount of wogonin in the composition depends on the composition type and can be varied such that the desired doses described herein are administered. Thus, in some embodiments, the compositions described herein include wogonin in an amount of about 0.01% to about 99% by weight of the total mass of the composition, including all integers within the specified range. In one embodiment, wogonin is about 0.01% to about 75% of the total mass of the composition, including all integers within the specified range. In another embodiment, wogonin is about 0.01% to about 50% of the total mass of the composition, including all integers within the specified range. In another embodiment, wogonin is about 0.01% to about 30% of the total mass of the composition, including all integers within the specified range. In another embodiment, wogonin is about 0.01% to about 10% of the total mass of the composition, including all integers within the specified range. In another embodiment, wogonin is about 0.1 to about 5% of the total mass of the composition, including all integers within the specified range. In another embodiment, wogonin is about 0.01% to about 1% of the total mass of the composition, including all integers within the specified range.

In some embodiments, wogonin is administered to a patient in a combination of a therapeutically effective amount of a secondary agent or a third agent. The secondary agent can be any pharmacologic agent known or suspected to be of benefit in the treatment or prevention of pain in a subject. For example, the secondary agent is a secondary pain relieving agent. Secondary pain relieving agents are well-known to those of ordinary skill in the art. Non-limiting examples of such agents include aspirin, acetaminophen (tylenol) or other aspirin-like drugs called nonsteroidal anti-inflammatory drugs (nsaids), weak narcotics such as codeine (tylenol with codeine), hydrocodone (vicodin or lortab), percocet, percodan or propoxyphene (darvon), strong opioids such as morphine, demerol, dilaudid, fentanyl (duragesic patches) and methadone.

Additional non-limiting examples of therapeutic agents suitable for use in the pharmaceutical compositions provided herein include: anti-inflammatory and antirheumatic active drug substances, such as, for example: butylpyrazolidine, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicam, piroxicam, tenoxicam, droxicam, lornoxicam, meloxicam, methotrexate, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine or bucillamine.

Additional therapeutic agents can include analgesics, such as, for example: opioids, natural opium alkaloids, morphine, opium, hydromorphone, nicomorphine, oxycodone, dihydrocodone, diamorphine, tapentadol, papaveretum, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, or ziconotide.

Additional therapeutic agents can include anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, rem ifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocaine, butanilicaine, cinchocaine, etidocaine, articaine, ropivacaine, levobupivacaine, esters of benzoic acid, cocaine, other local anaesthetics, such as, for example: ethyl chloride, dyclonine, phenol, or capsaicin.

Described below are examples of the embodiments, compositions, and methods described herein and are not intended to limit the scope of the invention further described in this disclosure.

EXAMPLES

Example 1. Wogonin Treatment of a Mouse Model of Osteoarthritis Formulated as a Cream The use of wogonin for the treatment of osteoarthritic (OA) pain was investigated. Specifically, the benefit of using small doses of wogonin applied topically in a cream with penetration enhancers was investigated. The cream formulation shown in Table 2 was used in this study. An additional exemplary cream formulation for administering wogonin is provided in Table 3.

An OA mouse model was used to determine the efficacy of wogonin treatment. OA-like disease was induced by surgical destabilization of the medial meniscal ligament (DMM) of laboratory mice. Repair of the knee was assessed using the Modified Mankin Score which is widely accepted as the way to objectively compare OA progression by histological evaluation of a knee joint (See Larkin D J et al., Frontiers in physiology. 2013; 4:121 and Mankin H J. The New England journal of medicine. 1974; 291(24):1285-92).

The mice were housed in activity wheel cages linked to a computer for activity tracking throughout the duration of the experiment. Twenty-four hours after surgical intervention the following treatments were applied topically to the affected knee: 0.00000142 g wogonin (500 µM wogonin) (n=6); 0.0000000028 g wogonin (10 µM wogonin) (n=6); and 10 µl vehicle (n=6). Treatment was applied every third day for 28 days.

TABLE 2

Exemplary Cream Composition

| Ingredient | Percent by weight |
| --- | --- |
| Water | ≥1% |
| Cetearyl Alcohol | ≥1% |
| Caprylic/Capric Triglyceride | ≥1% |
| Glycerin | ≥1% |
| Ethoxydiglycol | ≥1% |
| Glyceryl Stearate | ≥1% |
| PEG-100 Stearate | ≥1% |
| Stearic Acid | ≥1% |
| Butylene Glycol | ≥1% |
| Dimethicone | ≥1% |
| Mentha Piperita (Peppermint) Oil | ≥1% |
| Prunus Amygdalus Dulcis (Sweet Almond) Oil | ≥1% |
| Hydroxyethyl Acrylate/ Sodium Acryloyldimethyl Taurate Copolymer | ≤1% |
| Ceteareth-20 | ≤1% |
| Dimethyl Sulfone | ≤1% |
| Squalane | ≤1% |
| Phenoxyethanol | ≤1% |
| Caprylyl Glycol | ≤1% |
| Acrylates/C10-30 Alkyl Acrylate Crosspolymer | ≤1% |
| Xanthan Gum | ≤1% |
| Ethylhexylglycerin | ≤1% |
| Hexylene Glycol | ≤1% |
| Tetrasodium Glutamate Diacetate | ≤1% |
| Polysorbate 60 | ≤1% |
| Sorbitan Isostearate | ≤1% |
| Aloe Barbadensis Leaf Juice | ≤1% |
| Menthol | 0.1% |
| Wogonin (10 µM or 500 µM) | 0.0003 or 0.015% |

TABLE 3

Exemplary Cream Composition

| Ingredient | Weight | Weight % |
| --- | --- | --- |
| Dimethyl sulfone | 0.12 g | 5.1 |
| Polypropylene glycol (Sigma PHR 1051) | 0.027 g | 1.1 |
| Peppermint oil | 0.028 g | 1.1 |
| Shea butter | 1.2 g | 51 |
| Coconut oil | 0.6 g | 26 |
| Double distilled water | 0.36 g | 15 |

Seven days after starting the experiment, the mice receiving vehicle exhibited significantly higher wheel use than control. Mice receiving 10 µM and 500 µM wogonin exhibited significantly higher wheel use than control or vehicle alone. By day 14 mice receiving the vehicle still exhibited significantly higher wheel use than control. However, mice receiving 10 µM wogonin exhibited higher activity wheel use than those receiving 500 µM. At day 28 this pattern was repeated. The results are summarized in Table 4.

TABLE 4

| Summary of Activity Wheel Data. | |
| --- | --- |
| Treatment | Average Wheel Use |
| Control (no treatment) Day 7 | 6100 |
| Vehicle Day 7 | 10001* |
| Wogonin 500 µM Day 7 | 12608** |
| Wogonin 10 µM Day 7 | 12443** |
| Control (no treatment) Day 14 | 6300 |
| Vehicle Day 14 | 11191* |
| Wogonin 500 µM Day 14 | 17910** |
| Wogonin 10 µM Day 14 | 22000*** |
| Control (no treatment) Day 28 | 4500 |
| Vehicle 28 | 13152* |
| Wogonin 500 µM Day 28 | 16528* |
| Wogonin 10 µM Day 28 | 19358** |

* and ** mean P > 0.05

Biomarker Expression and Mankin Scores

While the wheel use data were encouraging, inhibiting inflammation alone and blocking pain, is insufficient to block the progression of OA. At the conclusion of the experiment (day 28) mice were sacrificed, knees collected, fixed and studied for Modified Mankin score and HtrA1 expression as previously reported in Spencer K MS and Jeffrey Z Kartchner W. *Journal of Arthritis*. 2015; 04(03). HtrA1 is the first in the biomarker cascade that is associated with OA progression.

Figure 2:
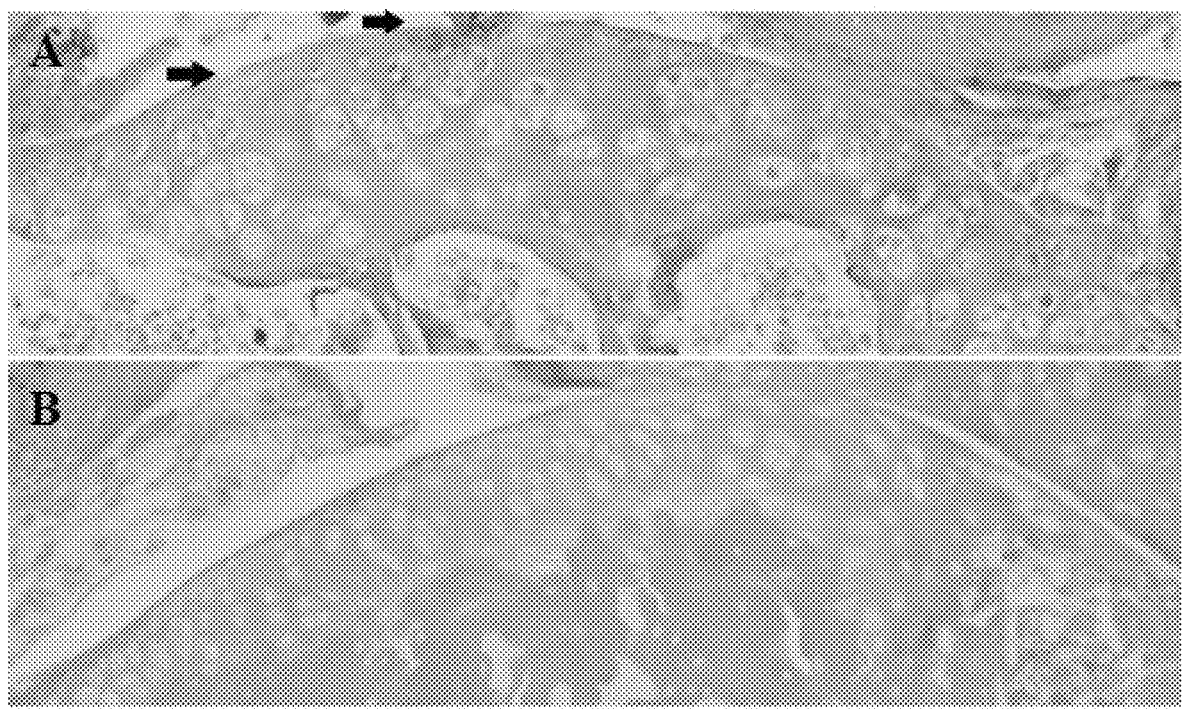
FIG. 2 is a histological staining of HtrA1 in mouse knee joints following DMM surgery; panel A represents mice subsequently treated with vehicle and panel B represents mice subsequently treated with 10 μM wogonin.

As shown in FIG. 1, a pharmacologic dose of wogonin rescues a joint subject to knee destabilization surgery. Mouse knee OA was induced by surgical destabilization of the medial meniscal ligament (DMM surgery) and mice were treated with 10 µM of wogonin. Controls were DMM plus vehicle. The Modified Mankin score of OA was statistically (p>0.05) lower in mice given the 10 µM wogonin treatment. Similar results were observed with lower doses. As shown in FIG. 2, wogonin inhibited HtrA1 expression as assessed my immunohistochemical staining in knee joints subjected to DMM surgery. Control/vehicle mice (A) exhibited ubiquitous staining of HtrA1 in chondrocytes. Note the fissure and rough articular cartilage surface (see arrows) in the control knee. Expression of HtrA1 was essentially absent in mouse knees treated with 10 µM wogonin (B.) There were no fissures noted and articular cartilage surface was essentially normal.

The modified Mankin scores (FIG. 1) and HtrA1 expression (FIG. 2) of wogonin treated knees followed a similar pattern as activity wheel data in that a decreased dosage of wogonin offered additional protection against OA. The idea that a modest amount of anti-inflammatory, such as wogonin to treat OA pain and reverse the OA disease process is counter-intuitive to the current thinking. Our study demonstrated that a lower dose of wogonin (10 µM compared to 500 µM) provided greater benefit in reducing the progression of OA. Indeed, we have observed that a dose of 1 µM wogonin applied topically is sufficient to significantly reduce OA as measured by Modified Mankin score. We have further observed that dosages below 1 µM wogonin are insufficient to have an effect. Dosages above 500 µM and there is too much suppression of inflammation and biomarkers. Thus, against conventional wisdom, providing a modest dose of an anti-inflammatory allows chondrocytes to return to homeostasis and exhibit cartilage repair/homeostasis.

Example 2. Wogonin Treatment of a Mouse Model of Osteoarthritis Formulated in a Cream or in a Liquid A second experiment using small doses of wogonin applied topically either in DMSO or in a cream with penetration enhancers was conducted. The cream formulation provided in Table 1 was used. In this study, OA was induced by DMM surgery. Twenty four hours after surgery treatment was applied to the affected knee. The treatments included 0.00000142 g wogonin in 10 µl DMSO (500 µM wogonin) applied to the skin at the location of patellar tendon (n=5); 10 µl DMSO applied to the skin at the location of patellar tendon (n=5); 0.0000000028 g wogonin (10 µl G2 Cream E/10 µM wogonin) to the skin at the location of the patellar tendon (n=5). Treatment was applied every third day for 28 days. Immediately after surgery, mice were placed in an activity wheel cage in which wheel use was recorded on a computer. Seven days after starting the experiment, the mice treated receiving either wogonin in DMSO or in a cream exhibited significantly higher wheel use than DMSO only. By day 14 mice receiving the cream still exhibited significantly higher wheel use while there was no difference between the DMSO or DMSO+wogonin treatments. At day 28 this pattern was repeated. The results are summarized in Table 5.

TABLE 5

| Summary of Activity Wheel Data | |
| --- | --- |
| Treatment | Average |
| Wogonin + DMSO Day 7 (500 µM) | 12608* |
| DMSO Day 7 | 9617 |
| Cream E Day 7 (10 µM) | 12443* |
| Wogonin + DMSO Day 14 | 15191 |
| DMSO Day 14 | 17910 |
| Cream E Day 14 | 22000* |
| Wogonin + DMSO Day 28 | 15492 |
| DMSO 28 | 16528 |
| Cream E Day 28 | 19358* |

Biomarker and Mankin scoring of knees followed a similar pattern, such that a higher dose of wogonin is beneficial initially but the lower dose remained beneficial throughout the experiment. From these data we conclude that an ideal dose for wogonin would be between 1 µM to 500 µM. Again, below 1 µM and there would be insufficient wogonin to have an effect. Above 500 µM and there would be too much suppression of inflammation and ceramides. TGF-β1 is inhibited and chondrocytes can't return to homeostasis, leading to cartilage repair.

Example 3. Roll-On Formulation for the Administration of Wogonin

An exemplary roll-on formulation for the administration of wogonin is provided in Table 6.

TABLE 6

| Exemplary Roll-on Composition |
| --- |
| Ingredient |
| Water |
| Alcohol |
| Caprylic/Capric Triglyceride |
| Propanediol |
| Ethoxydiglycol |
| Mentha Piperita (Peppermint) Oil |
| Dimethicone |
| Cetearyl Alcohol |
| Glyceryl Stearate |
| Potassium Olivoyl Hydrolized Oat Protein |
| Cetyl Alcohol |
| Xanthan Gum |

TABLE 6-continued

Exemplary Roll-on Composition

| Ingredient |
| --- |
| Phenoxyethanol |
| Caprylyl Glycol |
| Glyceryl Oleate |
| Sclerotium Gum |
| Lecithin |
| Ethylhexylglycerin |
| Hexylene Glycol |
| Pullulan |
| Menthol |
| Sodium Phytate |
| Wogonin |

Example 4. Application of Wogonin Cream and Knee Joint Health in Osteoarthritis Methods Mice and Joint Destabilization Procedure Seventeen, 28 day old C57BL/6 mice (treatment n=12), (sham n=5) were randomized for gender and a destabilization of the medial meniscus (DMM) procedure was performed similar to previously described (see Larkin D J et al., Frontiers in physiology. 2013; 4:121 and Mankin H J. The New England journal of medicine. 1974; 291(24):1285-92). Briefly, mice were anesthetized using isoflurane gas supplemented with room air and skin surrounding the right knee joint was prepped by clipping the fur and washing with an iodine surgical scrub followed by 70% alcohol. The remainder of the procedure was performed under a Wild Heerbrugg 355110 (Wild Heerbrugg AG, Switzerland) surgical microscope using sterile technique. The medial meniscotibial ligament was exposed by blunt dissection and the joint area was visualized. The meniscotibial ligament was subsequently transected using a number 11 scalpel to allow the displacement of the medial meniscus. Displacement of the meniscus was confirmed visually. The joint capsule and skin were both closed using 7-0 absorbable Vicryl suture (Ethicon, Inc., Somerville, NJ, USA). These procedures were conducted under a protocol 16-0501 approved by the Brigham Young University IACUC.

Cream Preparation

Treatment Cream was Arthritis Wonder® containing 10 µM wogonin. The Sham Cream was essentially Arthritis Wonder® without wogonin. Specifically, a 450 ml batch consisted of 384 ml double distilled water, 0.128 g dimethyl sulfone (MSM), 30.9 ml polyethylene glycol, 35.5 ml peppermint oil, 0.64 g coconut oil and 1.28 g shea butter as shown in Table 7.

TABLE 7

Test Cream Composition

| Ingredient | Amount | Weight % |
| --- | --- | --- |
| Dimethyl sulfone | 0.128 g | 0.03 |
| Polyethylene glycol 400 | 30.1 ml | 7.67 |
| Peppermint oil | 35.5 ml | 7.05 |
| Coconut oil | 0.64 g | 0.14 |
| Shea butter | 1.28 g | 0.28 |
| Water | 384 ml | 84.83 |

Tissue Preparation

Twenty-eight days post-surgery mice were euthanized and right knees were harvested and fixed in 4% paraformaldehyde, before decalcification and embedding in paraffin as previously described (see Larkin D J et al., Frontiers in physiology. 2013; 4:121 and Mankin H J. The New England journal of medicine. 1974; 291(24):1285-92)). Knees were sectioned and the corresponding sections were stained with Safranin-O and fast green as previously described (Larkin et al., 2013). Photographs of joint tissue were taken at 10× and 20× magnification using CellSens® software with an Olympus DP72 digital camera associated with an Olympus BX51 light microscope.

Joint Health Analysis

OA Scoring The Osteoarthritis Research Society International (OARSI) (see Glasson, S. S., et al., 2010) scoring system was used to assess OA severity as previously described (see Holt, D. W., et al., Osteoarthritis-like changes in the heterozygous sedc mouse associated with the HtrA1-Ddr2-Mmp-13 degradative pathway: a new model of osteoarthritis. Osteoarthritis Cartilage, 2012. 20(5): p. 430-9).

Cyst-Like Lesions Cyst-like lesions were counted at 10× magnification using ImageJ as previously described (see Zhang, Z. J., J. Beckett, and L. Schon, Cyst-Like Lesions at Chondro-Osseous Junction. Calcified Tissue International, 2017. 101(5): p. 549-552).

Immunohistochemistry

Immunohistochemistry (IHC) for NFκβ on slides representing serial sections of mouse knee joints from all animals as previously described (see Zhang, H. X., et al., Renal-protective effect of thalidomide in streptozotocin-induced diabetic rats through anti-inflammatory pathway. Drug Design Development and Therapy, 2018. 12: p. 89-98). Briefly, slides were deparaffinized and then blocked with 5% bovine serum albumin for 1 h. Rabbit polyclonal primary antibody against NFκβ (ab16502 Abcam, Cambridge, MA, United States) at a 1:200 dilution; Mmp-13 (ab39012 Abcam, Cambridge, MA, United States) at a 1:200 dilution; TGF-β1 (ab64715 Abcam, Cambridge, MA, United States) at a 1:100 dilution. The antibodies was applied to specimens, and incubated overnight at 4° C. On the second day, slides were rinsed with PBS and incubated with a goat anti-rabbit biotinylated secondary antibody (ab64256 Abcam, Cambridge, MA, United States). Slides were rinsed with PBS and then incubated with an avidin/biotin ABC mix (Vectastain elite ABC Kit). After a third rinse, a color reaction was initiated using a peroxidase substrate (Vector Labs, Nova-RED). Negative controls were prepared by staining without the addition of primary antibody. Differences in staining intensity were compared qualitatively with WT controls. Blind counting of stained cells was performed using ImageJ (NIH, Bethesda, MD, United States).

Cell Culture

Human chondrocytes (TC28a2 Sigma-Aldrich, St. Louis, MO, USA) were cultured in EmbryoMax® DMEM (SLM-120 B Millipore, St. Louis, MO, USA) supplemented with 10% Fetal Calf Serum (F-2442-50 ML Sigma-Aldrich, St. Louis, MO, USA) to 80% confluence. Treatments consisted of:

1. Untreated plate: Remove old media and replace with 10 mL fresh media. Incubate 4 hours. Remove media, rinse 3× with PBS and collect total RNA according to manufacturer's protocol (R1054 ZYMO Research, Irvine, CA, USA).
2. Treat with 10 µM wogonin (dissolved in DMSO). Remove old media and replace with 10 mL conditioned media containing wogonin. Incubate 4 hours. Remove media, rinse 3× with PBS and collect total RNA according to manufacturer's protocol (R1054 ZYMO Research, Irvine, CA, USA).

3. Treat with 1 ng/mL IL-1β (dissolved in dds water). Remove old media and replace with 10 mL conditioned media containing IL-1β. Incubate 4 hours. Remove media, rinse 3× with PBS and collect total RNA according to manufacturer's protocol (R1054 ZYMO Research, Irvine, CA, USA).
4. Treat with 10 μM wogonin; wait 1 hour and add 1 ng/mL IL-1β, incubate 4 hours. Remove old media and replace with 10 mL conditioned media containing wogonin. Incubate 1 hour. Add 10 μL 1 ng/mL IL-1β. Pipet media up and down in cell culture dish 3× gently to mix. Incubate 4 hours. Remove media, rinse 3× with PBS and collect total RNA according to manufacturer's protocol (R1054 ZYMO Research, Irvine, CA, USA).

cDNA was made from total RNA according to manufacturer's protocol (1725038 BIO-RAD, Hercules, CA, USA).

Quantitative Real-time Polymerase Chain Reaction (qRTPCR) was performed using the Life Technologies One Step Plus Sequence Detection System and Software (Life Technologies). SYBR-green-based PrimeTime assays (IDT) were used to detect human TGF-β1 and BBS 3. Primer sequences were:

```
TGF-β1 F
                             (SEQ ID NO: 1)
5'-GCACGTGGAGCTGTACCAGA-3'

TGF-β1 R
                             (SEQ ID NO: 2)
5'-GCCGGTAGTGAACCCGTTG-3'

BBS 3 F
                             (SEQ ID NO: 3)
5'-ACCAGAAAAACTGCCTGCTCT-3'

BBS 3 R
                             (SEQ ID NO: 4)
5'-AGCCCAAGGCACAAAACATGA-3'
```

Statistical Analysis

Statistical significance of the Mankin and OARSI scores for the treated and untreated 28-day mice were obtained using a two-way ANOVA test. Differences in cyst-like lesions (CLLs) and NFκβ stained cells were obtained determined by the Mixed Models (ANOVA) statistical method. All statistical analyses were conducted by the Statistics Department at Brigham Young University.

Results

Osteoarthritis Assessment

Figure 3:
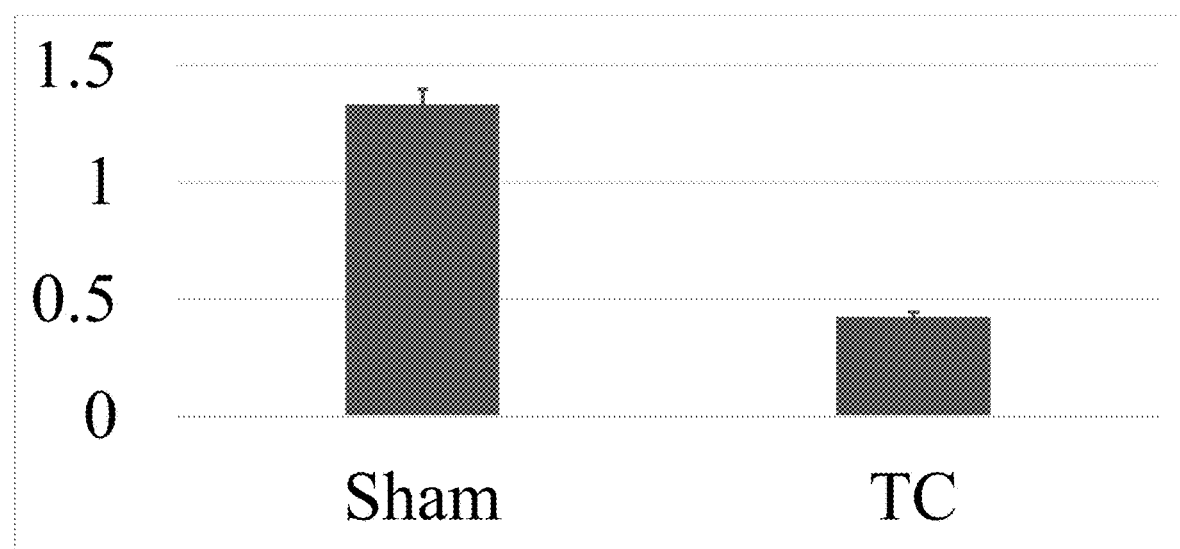
FIG. 3 is a bar graph comparing OARSI scores of mice treated with a test cream composition (TC) versus a sham cream composition (sham) according to Table 7 after DMM knee destabilization surgery (*p>0.05).
Figure 4:
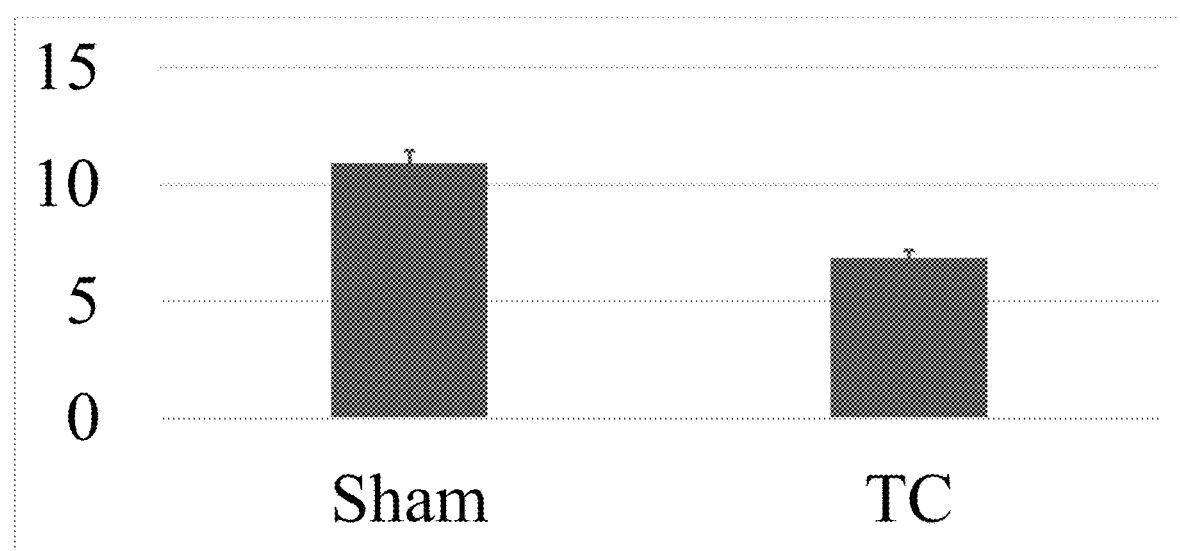
FIG. 4 is a bar graph comparing the number of cyst-like lesions in mice treated with a test cream composition (TC) versus a sham cream composition (sham) according to Table 7 after DMM knee destabilization surgery (*p>0.01).
Figure 5:
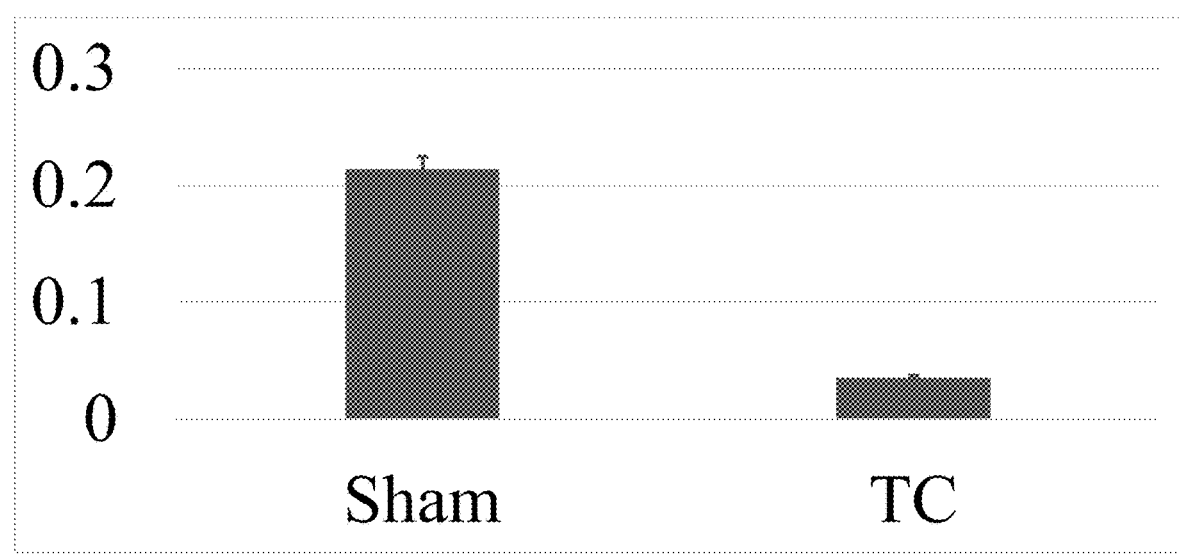
FIG. 5 is a bar graph that compares the number of NFκβ positive cells from the articular cartilage of mouse knee joints treated with a test cream composition (TC) versus a sham cream composition (sham) according to Table 7 after DMM knee destabilization surgery (*p>0.01).
Figure 6:
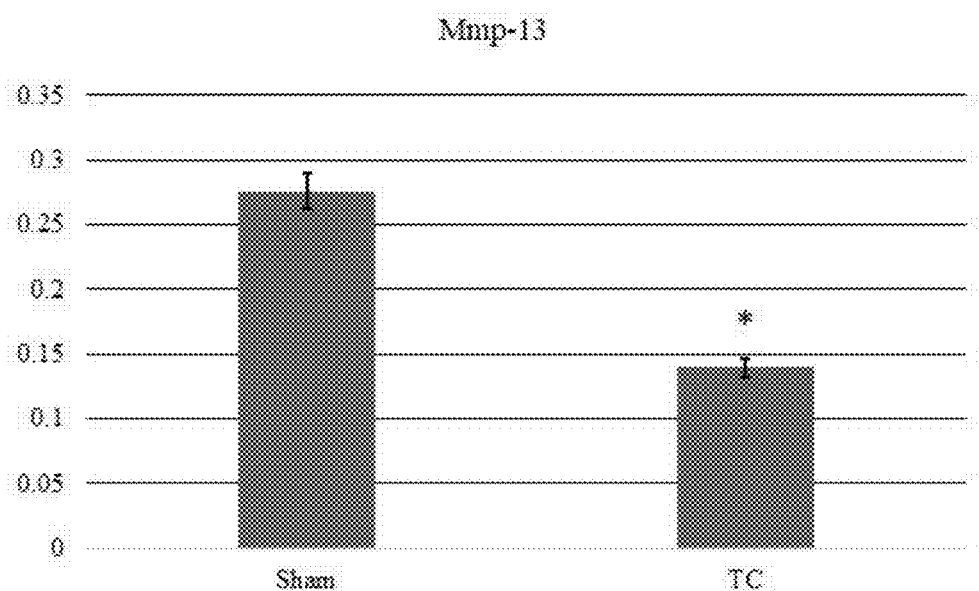
FIG. 6 is a bar graph that compares the number of Mmp-13 positive cells from the articular cartilage of mouse knee joints treated with a test cream composition (TC) versus a sham cream composition (sham) according to Table 7 after DMM knee destabilization surgery (*p>0.01).
Figure 7:
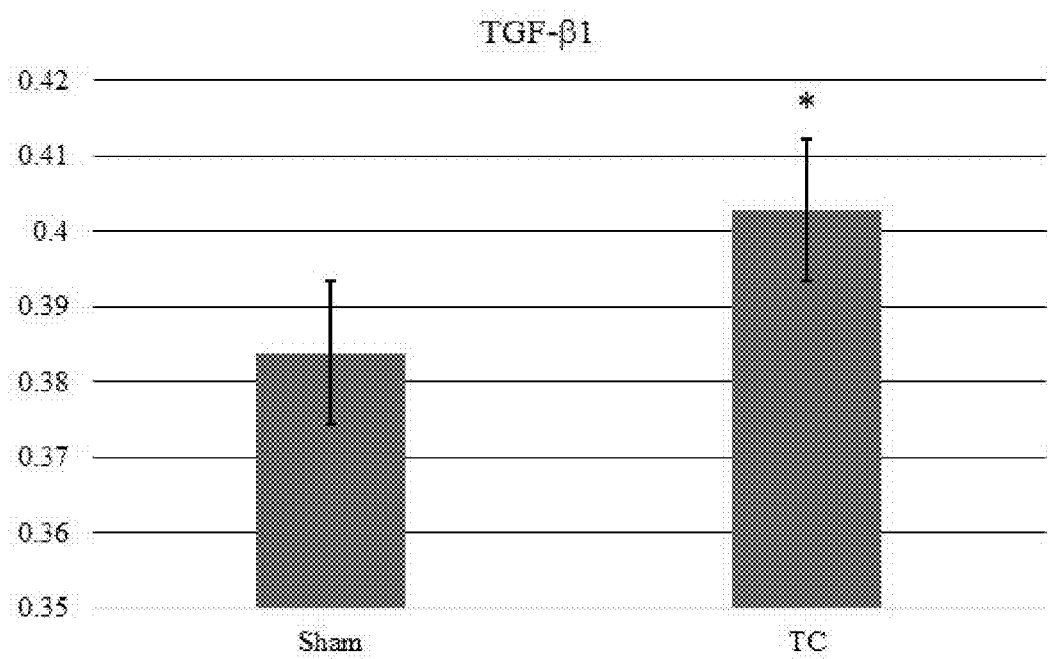
FIG. 7 is a bar graph that compares the number of TGF-β1 positive cells from the articular cartilage of mouse knee joints treated with a test cream composition (TC) versus a sham cream composition (sham) according to Table 7 after DMM knee destabilization surgery (*p>0.05).
Figure 8:
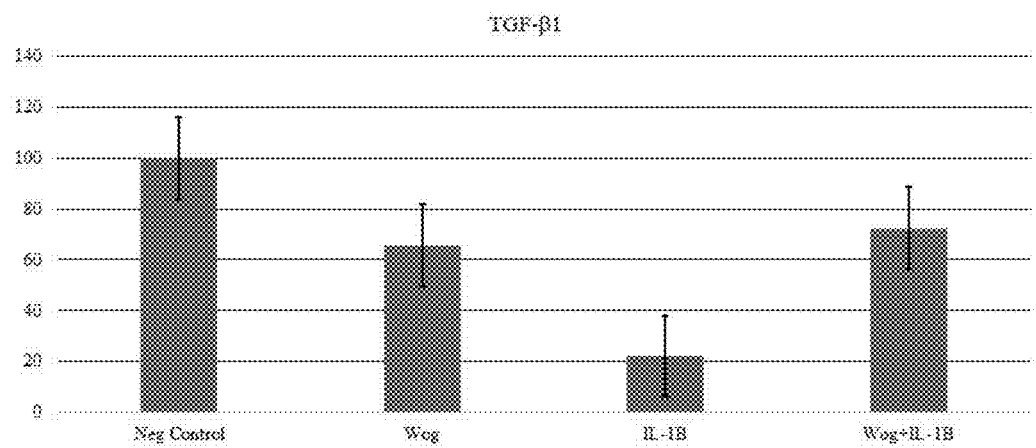
FIG. 8 is a bar graph that compares TGF-β1 PCR product after quantitative RTPCR using RNA from human chondrocytes treated with a 10 μM wogonin, IL-1β or wogonin pre-treatment followed by IL-1β versus no treatment.
Figure 9:
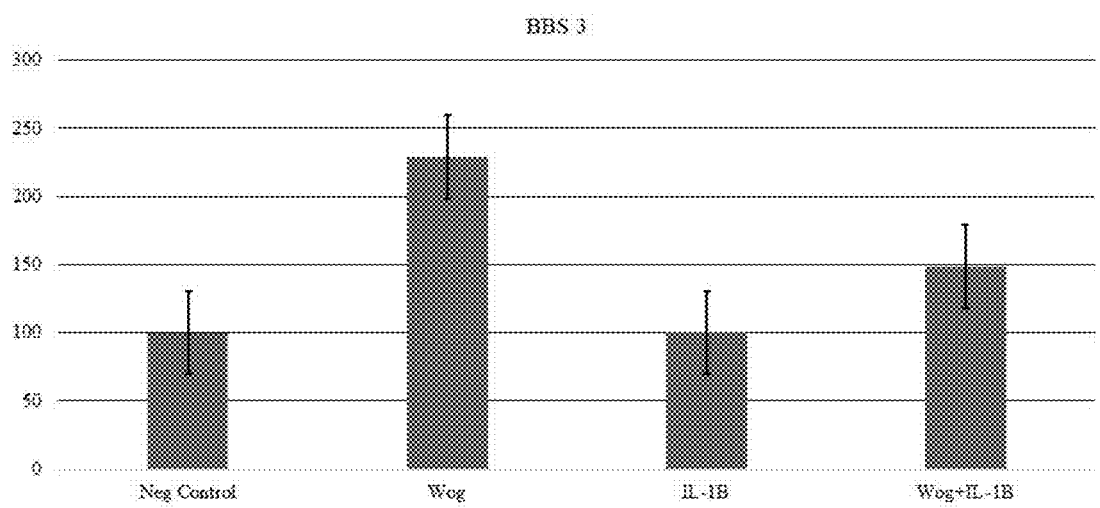
FIG. 9 is a bar graph that compares BBS 3 PCR product after quantitative RTPCR using RNA from human chondrocytes treated with a 10 μM wogonin, IL-1β or wogonin pre-treatment followed by IL-1β versus no treatment.

The Osteoarthritis Society International (OARSI) developed a more holistic procedure for assessing OA in joints in place of the more traditional Mankin scoring system (see Glasson, S. S., et al., *The OARSI histopathology initiative—recommendations for histological assessments of osteoarthritis in the mouse.* Osteoarthritis Cartilage, 2010. 18 Suppl 3: p. S17-23). OARSI scoring was done on knee sections stained with Safranin-O to assess the joint health. The Mice treated with the test composition according to Table 7 (TC) had an average score of 0.426 while the mice treated with a sham cream (SC) had an average score of 1.332 (FIG. 3). The TC treated mice had a significantly lower OARSI score $P<0.05$ compared to SC treated mice when analyzed by a Two-Way ANOVA test. The use of TC significantly decreased the OARSI score. *$P<0.05$ Cyst-Like Lesions A newly identified marker for joint health is the lack or presence of cyst-like lesions (CLL) in the chondro-osseous junction which consists of tidemark, the calcified zone of cartilage, and cement line (see Zhang, Z. J., J. Beckett, and L. Schon, *Cyst-Like Lesions at Chondro-Osseous Junction.* Calcified Tissue International, 2017. 101(5): p. 549-552). The number of CLLs were counted in Safranin O/F Fast Green stained knee sections of TC and SC treated mice. Mice receiving TC exhibited an average of 6.2 CLLs compared to 11 in the SC mice (FIG. 4). There were significantly fewer CLLs in the TC mice compared to SC mice ($p<0.01$) as determined by the Mixed Models (ANOVA) statistical method. The use of TC significantly decreased the number of CCLs. *$P<0.01$ Immunohistochemical Analysis Immunohistochemistry was performed to assess the interaction of wogonin with primary cilia on sections of mouse knee joints from TC and SC treated mice. Slides were stained with antibody against NFκβ, Tgf-β1 or Mmp-13. The qualitative results of the immunohistochemical staining was analyzed quantitatively by calculating the percentage of cells staining positive for the respective biomarker and the total number of chondrocytes in a defined 200×900 pixel area of articular cartilage immediately distal to the tibial plateau. All quantitative analyses were performed using ImageJ (National Institutes of Health, Bethesda, MD). We observed significantly fewer chondrocytes staining positive for activated NFκβ using an ANOVA test to detect differences in the mean percentages of positive staining for NFκβ and mean chondrocyte counts between the TC and SC samples (FIG. 5). The use of TC significantly decreased the number of cells staining for NFκβ. *$P<0.01$ We observed significantly more chondrocytes staining positive for activated TGF-β1 using an ANOVA test to detect differences in the mean percentages of positive staining for TGF-β1 and mean chondrocyte counts between the TC and SC samples (FIG. 7). The use of TC significantly increased the number of cells staining for TGF-β1. *$P<0.05$ We observed significantly fewer chondrocytes staining positive for activated Mmp-13 using an ANOVA test to detect differences in the mean percentages of positive staining for Mmp-13 and mean chondrocyte counts between the TC and SC samples (FIG. 5). The use of TC significantly decreased the number of cells staining for Mmp-13. *$P<0.01$ We observed an 80% drop in gene expression of TGF-β1 in human chondrocytes after exposure to IL-1β as assayed by real time PCR. However, there was less than a 40% drop if cells were pre-treated with wogonin. Wogonin alone gave a similar result.

We observed a 125% increase in gene expression of BBS 3 in human chondrocytes after exposure to wogonin. IL-1β had no effect on BBS 3 gene expression but did lower the wogonin response by almost half.

Fewer CLLs, lower OARSI scores with less NFκβ, Mmp-13 and more Tgf-β1 activation in spite of significantly greater running wheel use after knee destabilization surgery suggests that TC, containing a low level of wogonin, blocks the primary cilia pathway of cartilage degradation to promote cartilage homeostasis.

BBS 3 is a component of the BBSome (see Zhang et al., Bardet-Biedl syndrome 3 (Bbs3) knockout mouse model reveals common BBS-associated phenotypes and Bbs3 unique phenotypes. PNAS 108 (51): 20678-20683). BBS3 is required for the BBSome to enter cilia. The BBSome can play a role in taking ciliary proteins to cilia or removing them from cilia. Thus, an increase in BBS3 in the presence of cilia could be an anti-inflammatory response depending on what the BBSome is trafficking and in which direction. Regardless, these results clearly demonstrate that wogonin has a significant effect (1.25 fold increase in BBS 3 expression) on primary cilia. A modest dose of wogonin in a topical cream promotes joint health and represents a novel treatment for the disease.

We demonstrate a significant reduction in OARSI score and CLLs in mice treated with topical application of wogonin via Arthritis Wonder® after knee destabilization surgery. We further demonstrate that primary cilia are intimately involved in maintaining cartilage homeostasis and evidenced by a significant reduction in the number of cells staining positive for NFκβ or increase in TGF-β1, both regulated by primary cilia, associated with treatment. The treatment of OA must take into account the role that primary cilia play in joint homeostasis and not rely solely on blocking inflammation. We demonstrate that wogonin exhibits protective effects on chondrocytes holistically by acting through primary cilia and that topical application of wogonin attenuates OA progression, treating the disease. This is a novel pathway not previously attributed to wogonin and explains why it has a powerful holistic benefit to an osteoarthritic joint when applied topically in a cream.

Although the invention herein has been described in connection with described embodiments thereof, it will be appreciated by those skilled in the art that additions, modifications, substitutions, and deletions not specifically described may be made without departing from the spirit and scope of the invention as defined in the appended claims. It is, therefore, intended that the foregoing detailed description be regarded as illustrative rather than limiting, and that it be understood that it is the following claims, including all equivalents, that are intended to define the spirit and scope of this invention.

The invention claimed is:

1. A method of treating topical pain, comprising administering to a patient in need thereof a composition with a therapeutically effective amount of 5,7-dihydroxy-8-methoxy-2-phenylchromen-4-one of 1 µM to 500 µM with a cosmetically or dermatologically acceptable carrier, the composition further comprising:
   a) 5.1% dimethyl sulfone,
   b) 1.1% polypropylene glycol,
   c) 1.1% peppermint oil,
   d) 51% shea butter,
   e) 26% coconut oil, and
   f) 15% water.

2. The method of claim 1, wherein the composition comprises one or more excipients selected from a surfactant, an emulsifier, a fat, a fatty acid, a triglyceride, a solvent, a thickener, a skin conditioning agent, a chelator, a fragrance, a penetration enhancer, and combinations thereof.

3. The method of claim 2, wherein the one or more excipients is selected from cetearyl alcohol, caprylic/capric triglyceride, glycerin, ethoxydiglycol, glyceryl stearate, peg-100 stearate, stearic acid, butylene glycol, dimethicone, prunus amygdalus dulcis (sweet almond) oil, hydroxyethyl acrylate, sodium acryloyldimethyl taurate copolymer, ceteareth-20, squalane, phenoxyethanol, caprylyl glycol, acrylates/c10-30 alkyl acrylate crosspolymer, xanthan gum, ethylhexylglycerin, hexylene glycol, tetrasodium glutamate diacetate, polysorbate 60, sorbitan isostearate, aloe barbadensis leaf juice, and menthol and combinations thereof.

4. The method of claim 1, wherein the 5,7-dihydroxy-8-methoxy-2-phenylchromen-4-one is 90% to 100% pure.

5. The method of claim 1, wherein the pain is selected from a musculoskeletal pain and arthritis pain.

6. The method of claim 1, wherein the administering step is locally to one or more arthritic joints of the patient.

7. The method of claim 6, wherein the administering step reduces inflammation within the arthritic joint.

8. The method of claim 1, wherein an expression of a ceramide is increased, TGF-β1 is increased, MMP-13 is decreased, HtrA1 is decreased, NFκB is decreased, and AGE is decreased within or proximally surrounding the arthritic joint, comprising cartilage and synovial fluid, compared to an arthritic joint not treated with the composition.

9. The method of claim 8, wherein the expression of cytokines HtrA1, MMP-13, NFκB and AGE are reduced by at least 20% and TGF-β1, ceramide, and BBS 3 are elevated by at least 20% compared to an arthritic joint not treated with the composition.

10. The method of claim 6, wherein the arthritic joint is an osteoarthritic joint.

11. The method of claim 1, wherein the composition is in a form of a liquid, rub, foam, cream, solution, emulsion, gel, spray, wipes, a lotion, or a patch or combinations thereof.

12. A method of treating musculoskeletal pain, comprising administering to a patient in need thereof a composition with a therapeutically effective amount of 5,7-dihydroxy-8-methoxy-2-phenylchromen-4-one of 1 μM to 500 μM with a cosmetically or dermatologically acceptable carrier, the composition further comprising:
a) 5.1% dimethyl sulfone,
b) 1.1% polypropylene glycol,
c) 1.1% peppermint oil,
d) 51% shea butter,
e) 26% coconut oil, and
f) 15% water.

13. The method of claim 12, wherein the composition is in a form of a liquid, rub, foam, cream, solution, emulsion, gel, spray, wipes, a lotion, or a patch or combinations thereof.

14. The method of claim 12, wherein the composition comprises one or more excipients selected from a surfactant, an emulsifier, a fat, a fatty acid, a triglyceride, a solvent, a thickener, a skin conditioning agent, a chelator, a fragrance, a penetration enhancer, and combinations thereof.

15. The method of claim 14, wherein the one or more excipients is selected from cetearyl alcohol, caprylic/capric triglyceride, glycerin, ethoxydiglycol, glyceryl stearate, peg-100 stearate, stearic acid, butylene glycol, dimethicone, prunus amygdalus dulcis (sweet almond) oil, hydroxyethyl acrylate, sodium acryloyldimethyl taurate copolymer, ceteareth-20, squalane, phenoxyethanol, caprylyl glycol, acrylates/c10-30 alkyl acrylate crosspolymer, xanthan gum, ethylhexylglycerin, hexylene glycol, tetrasodium glutamate diacetate, polysorbate 60, sorbitan isostearate, aloe barbadensis leaf juice, and menthol and combinations thereof.

16. The method of claim 12, wherein the 5,7-dihydroxy-8-methoxy-2-phenylchromen-4-one is 90% to 100% pure.

17. The method of claim 12, wherein the administering step is locally to one or more arthritic joints of the patient.

18. The method of claim 17, wherein the administering step reduces inflammation within the arthritic joint.

19. The method of claim 12, wherein an expression of a ceramide is increased, TGF-β1 is increased, MMP-13 is decreased, HtrA1 is decreased, NFκB is decreased, and AGE is decreased within or proximally surrounding the arthritic joint, comprising cartilage and synovial fluid, compared to an arthritic joint not treated with the composition.

20. The method of claim 19, wherein the expression of cytokines HtrA1, MMP-13, NFκB and AGE are reduced by at least 20% and TGF-β1, ceramide, and BBS 3 are elevated by at least 20% compared to an arthritic joint not treated with the composition.

21. The method of claim 17, wherein the arthritic joint is an osteoarthritic joint.

\* \* \* \* \*